United States Patent [19]

Bruns et al.

[11] Patent Number: 4,581,030

[45] Date of Patent: Apr. 8, 1986

[54] COLLAGEN REPLACEMENT PROTHESIS FOR THE CORNEA

[75] Inventors: Romaine R. Bruns, Norwood; Jerome Gross, Waban, both of Mass.

[73] Assignee: Massachusetts General Hospital, Boston, Mass.

[21] Appl. No.: 683,134

[22] Filed: Dec. 18, 1984

Related U.S. Application Data

[62] Division of Ser. No. 431,578, Sep. 30, 1982, Pat. No. 4,505,855.

[51] Int. Cl.$^4$ ............................................. A61F 2/14
[52] U.S. Cl. ................................. 623/5; 128/DIG. 8; 623/4
[58] Field of Search .................... 3/13, 1; 128/DIG. 8

[56] References Cited

U.S. PATENT DOCUMENTS 4,223,984  9/1980  Miyata et al. ............ 128/DIG. 8 X
4,298,004 11/1981  Schachar et al. ........ 128/DIG. 8 X
4,427,808  1/1984  Stol et al. ............................. 524/24

Primary Examiner—Richard J. Apley
Assistant Examiner—Alan W. Cannon
Attorney, Agent, or Firm—David G. Conlin; George W. Neuner

[57] ABSTRACT

This invention relates to a prosthetic replacement for the cornea and particularly to a transparent collagen material useful for making such a prosthesis and to methods for making such transparent collagen material. The prosthesis is preferably composed of a native, non-fibrilized, transparent collagen material formed from a soluble collagen solution by ultracentrifuging to form a pellet and fixing the same pellet, whereby the collagen material has less than 5% absorbance of light at 900 nm for a 5 mm thick sample and comprises polyhydroxyethylmethacrylate or vitrosin, in a range of from 0.01 to 50.0 percent by weight, based on the collagen protein.

4 Claims, 1 Drawing Figure

COLLAGEN REPLACEMENT PROTHESIS FOR THE CORNEA

This is a division of application Ser. No. 431,578 filed Sept. 30, 1982, now U.S. Pat. No. 4,505,855.

FIELD OF THE INVENTION

This invention relates to a prosthetic replacement for the cornea and particularly to a transparent collagen material useful for making such a prosthesis and to methods for making such transparent collagen material.

BACKGROUND OF THE INVENTION

Most synthetic polymer membranes are extruded from the cornea after intralamellar implantation. This is explained by their impermeability, both to water and metabolites, which causes desiccation of the corneal stroma anterior to the membrane. It has been suggested that an approach to the problem of finding a suitable corneal implant material is the use of collagen.

Collagen is a protein which constitutes about 20 to 30 percent of the total body protein in vertebrates. It is a fibrous protein and functions primarily as a supporting tissue and scaffolding for other proteins and cells. It is present throughout the body but exists in high concentrations in skin, tendon and bone.

Collagen is recovered from these tissues by a variety of techniques, the oldest known method being the boiling of the tissue in water which denatures some of the collagen and forms gelatin on cooling. For use as a biomaterial however, collagen must be recovered in native, undenatured form, i.e., with little or no destruction of the basic rigid triple helical structure (tropocollagen).

Undenatured native collagen is recovered principally by two methods, (a) solution by dissolving the collagen in acids, bases, salts or by enzyme digestion, in which instances the collagen becomes actually dissolved, and (b) extraction in solid, undissolved, fiber form (hereinafter "fibrous collagen) usually by the action of aqueous salt or minced, comminuted collagen raw material to produce a dispersion from which the solid is recovered by centrifugation, etc. Both the solution and extraction methods are described in the collagen art.

Collagen materials have been studied for many years and for many suggested uses. For example, Dunn et al, in *Science*, 157 pp. 1329-30 (1967), the disclosure of which is incorporated herein by reference, describe the use of collagen-derived membranes for corneal implantation. Dunn et al, in *Ophthalmic Surg.*, 2(1), pp. 9–11 (1971), the disclosure of which is incorporated herein by reference, described the use of collagen membranes for intralamellar corneal implants in experimental surgery. U.S. Pat. No. 4,268,131, the disclosure of which is incorporated herein by reference, describes a soft contact lens made from fibrous collagen and mixtures of such fiber with purified solubilized collagen. U.S. Pat. No. 4,223,984, the disclosure of which is incorporated herein by reference, describes soft contact lenses made from solubilized, defatted, cross-linked collagen, and/or chemically modified collagen. U.S. Pat. No. 4,164,559 describes a chemically modified membrane as a carrier for ophthalmic medication leaving no removable material after drug release. U.S. Pat. No. 4,233,360 describes a method for preparing non-mitigenic collagen and suggests its use for medical products such as sponges, prosthetic devices, films, membranes, sutures, etc. U.S. Pat. No. 4,279,812 describes a method for preparing macromolecular biologically active collagen and suggests its use for making implants for slow release of medication. See also Dunn et al., "Corneal Derived Membrane: Corneal Implantations," in *Biomaterials*, edited by Stark and Agarwal, Plenum Press, New York (1969) at pp. 195–199, the disclosure of which is incorporated herein by reference.

To date, no one to the knowledge of the present applicants has successfully produced a collagen material that can be used as a prosthetic replacement for the cornea. Typically collagen materials, although transparent when used in thin membranes, are not sufficiently transparent when made in a thickness suitable for use as a prosthetic replacement for the cornea.

Thus, there remains a desire for a native collagen material suitable for making a prosthetic replacement for the cornea.

SUMMARY OF THE INVENTION

The present invention provides a transparent native, non-fibrilized collagen material having an absorbance at a wavelength 900 nm of less than 5% in a sample 5 mm thick. This collagen material of the present invention is useful for prosthetic replacement of the cornea because of the high transparency and because it is a native material, and thus less susceptible to immunogenic responses.

The collagen material is preferably made by ultracentrifuging a cold collagen solution, i.e., centrifuging at about 80,000 or more times gravity, preferably at about 100,000–120,000 times gravity until the level of supernate is constant. The supernate is removed and the pellet is fixed by treating it to produce cross-linking between the molecules of collagen.

The collagen material of this invention can also be used for prosthetic replacement of other bodily tissues, such as nucleus pulposus, cartilage, and vitreous body.

DETAILED DESCRIPTION OF THE INVENTION

Figure 1:
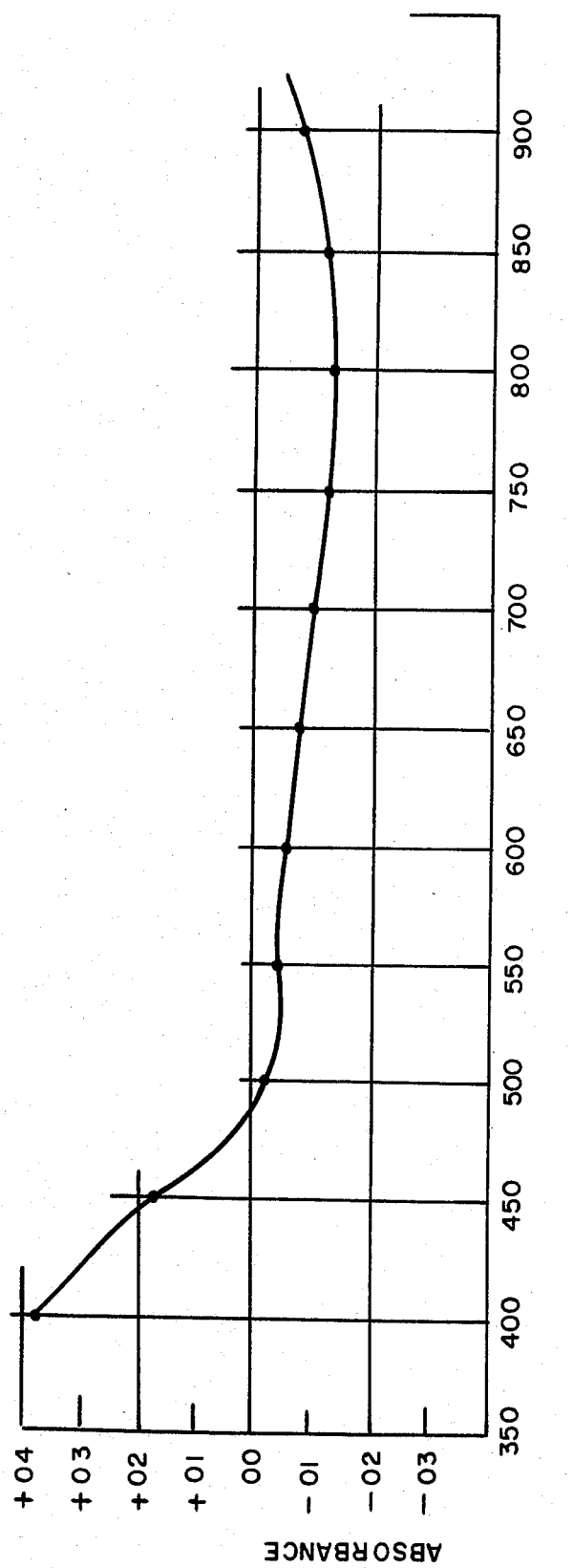
FIG. 1 is a graph of absorbance versus wavelength for a 5 mm thick sample of the collagen material of the present invention.

Prior to the present invention the use of collagen based materials in cases where transparency is important has been limited to use as thin membranes, because prior art collagen materials were not sufficiently transparent for optical use except in such membrane from where the thinness made up for the lack of transparency.

The collagen material of the present invention, however, is a highly transparent, relatively hard non-fibrilized gel, and thus it is advantageous for use in corneal replacement. The collagen material of this invention is made from soluble native collagen. Preferably the collagen is first extracted from native materials such as skin, rat tail tendons, or tendons from other parts of mammals, by dissolution. As noted above, the method can involve dissolution in acids, bases, salts, or enzymatic dissolution. Preferably the collagen is derived by acidic dissolution of the natural source, e.g., by dissolution of rat tail tendon in acetic acid. Although the acid extract is commonly referred to as a "solution", its exact molecular make-up is not precisely known, and the molecular weight of collagen (usually about 300,000) is such that "solutions" of it may also have some properties usually associated with collodial dispersions. Thus, "solution" in this application is meant to include a uniform molecular dispersion, however else it may be categorized.

Preferably the native collagen solution is then treated to remove impurities and debris. Often this can simply be done by low gravity centrifugation, but other methods, such as filtration, precipitation, solvent extraction and other methods known in the art may be used to advantage in different cases to remove different contaminants. An important aspect is that the collagen contained in the solution is not denatured by or during the purification step. Typically, a solution of soluble collagen may be simply centrifuged in a clinical centrifuge at about 3000 to 4000 rpm to remove debris. The supernate from the centrifuging step may then be ultracentrifuged at about 40,000 rpm (greater than 100,000 g) for a period of time sufficient to form a constant size, transparent pellet. In some, cases where the solution has not been rendered completely pure and free of debris, a cloudy layer may form first, with the transparent gel pellet (containing the desired collagen material of this invention) forming over the first cloudy layer. The cloudy layer may be removed before or after fixation of the collagen.

The transparent pellet formed by ultracentrifuging is then fixed to form a rigid structure. It can be fixed by chemicals or by irradiation to form crosslinks in the gel. One method of chemically crosslinking the gel is to treat it with a fixing agent, many of which are known, such as a solution of formaldehyde and/or glutaraldehyde. However, any other well-known method for fixing the gel is suitable. After fixing, the gel becomes rigid and tough, having a leatherlike consistency when cutting it with a razor. The gel can then be cut, machined, or otherwise shaped as desired for a prosthesis.

The collagen gel thus prepared differs greatly from previously known collagens. A striking difference is the transparency. Instead of having to utilize thin layers in order to obtain lens material, the collagen gel produced in accordance with the present invention appears optically clear through thickness of one centimeter or more. The density, hardness and toughness are also much higher than previous native gels. Without asking to be bound by theory, it is believed that the reason for the unique properties of the present material is that the extremely high G centrifugation for extended periods (10 to 60 hours, preferably 20 to 40 hours) results in alignment of the collagen molecules in a particular direction with respect to the axis of rotation.

In a preferred embodiment of the invention, the soluble native collagen solution, prior to ultracentrifuging, is dialyzed against water to remove any salts or acids present. Dialyzing against water also tends to associate the molecules of collagen in an end to end configuration in long chains or strands. Pellets made from dialyzed collagen exhibit thin strand-like structure under electron microscopy.

The method of obtaining solubilized collagens from the crude collagen source, e.g. skin, tendon, hide, etc., is not critical, and some flexibility may be used in the selection of the particular tissue and the method applied thereto. The greater part of native collagen is insoluble, but can be solubilized in dilute acids, e.g. acetic acid; in bases e.g. NaOH; and in dilute aqueous salts, e.g. NaCl. Relatively low yields are typically obtained. Such processes are well known in the collagen extraction art, such as the references cited above.

Collagen tissue of young animal such as calfskin contains about 1–2% acid soluble collagen. This collagen may be extracted by treatment with aqueous acid (pH 2–4) solutions such as 0.1M acetic acid or 0.15 M citrate buffer (pH 3.6).

Alternatively, cattle skin, e.g. the corium layer of hide, may be soaked in 4% NaOH containing 0.2 M monomethylamine and 15% sodium sulfate for 10–15 days at room temperature. The hide is washed with water to remove bases and then extracted by stirring in 0.1 N acetic acid containing 0.1 M NaCl (pH 2.8). Almost all the hide is dissolved and a viscous solution will be obtained. This collagen may be precipitated by raising the pH to 4–5, collected by centrifugation and washed with water.

Collagen solutions thus obtained can be treated to remove any fat content. After dehydration with ethanol, the collagen is preferably treated with ethanol-ether (1:1), to produce defatted collagen. After air-drying, defatted collagen can be re-dissolved in an acidic aqueous solution, pH 2–4 to remove debris. If desired, the solution may be filtered through millipore filters up to 0.65 micron pore size. The collagen is precipitated at pH 4–5 and collected by centrifugation. Finally, this collagen is mixed with acid, so that 0.1 to 0.5% by weight, preferably 0.2 to 0.4% collagen gels in aqueous medium, at pH 2–4, are prepared for ultracentrifugation.

Collagen can be extracted from tissue by treatment with salt solutions, e.g. dilute aqueous NaCl, but the yields are poor as in the case of acid extraction, and this procedure is not generally recommended.

Enzymatic extraction may be carried out as follows: cleaned, de-haired hide or skin is cut into pieces of workable size and slurried in acidified water in the presence of a proteolytic enzyme (other than collagenase). Suitable enzymes are pepsin, trypsin, pronase, proctase, etc. Two fractions are obtained from this digestion, one an insoluble solid fraction which is discarded, and a solution or soluble fraction which is worked up as follows. The solution is brought to a pH of about 10.0 to denature the remaining active enzyme, and then neutralized to a pH of about 6.0–7.0. "Atelocollagen" precipitates at this pH leaving behind in solution (to be discarded) the digested telopeptides, and other contaminating proteins, and any saccharides, mucopolysaccharides, etc. The atelocollagen is usually further purified by repeating solubilization at pH 2–3 and reprecipitation at pH 6–7. The recovered collagen is then washed with ethanol to remove any lipid content and excess water in preparation for the solvent defatting process. The collagen is defatted by treatment with 1:1 ethanol-ethyl ether mixture and recovered as a viscous solid usually by cheesecloth filtering. It is then air-dried, and subsequently converted to a gel by solubilization in acidified water at a pH of about 3.0.

The pellet formed by the ultrafugation step contains between 0.5 and 20% collagen proteins, preferably about 1 to 8% collagen protein, most preferably about 4% collagen protein, with the balance water.

Other biocompatible materials can also be included in the prosthesis compositions of the percent invention, including polyhydroxyethylmethacrylate (poly-HEMA), vitrosin, a fibrous protein found in mammalian vitreous humor, and other additives known in the art, such as plasticizers, to reduce brittleness and increase flexibility, silicones to extend the collagen, and other materials known in the art. Such materials may tend to prevent cell migration into the prosthesis. Such materials may be incorporated in any amount which does not adversely affect transparency of the resultant compositions, or cause loss of biocompatibility, e.g. the material may cease to be non-immunogenic. Preferably, the additional material is added in amounts of 0.01 to 50 percent, more preferably from about 0.9% to about 20% by weight.

The prosthesis material of the present invention may be utilized in man or animals by surgical implantation.

One source of commercially prepared collagen suitable for the practice of the present invention is the Collagen Corporation which markets a highly purified, pepsinized calf-skin soluble collagen under the trademark Vitrogen. Since this material is already purified, the collagen gels of the present invention can be made directly by ultracentrifugation.

The invention will be further illustrated by the following examples. Unless otherwise stated, all temperatures are in °C. and all percents are by weight.

EXAMPLE 1

Five (5) fresh tails were obtained from 250-275 g albino rats. The tendons were removed and immediately placed in a petri dish of Tyrode's solution (a commercially available salt solution). The tendons (2.0 grams) were transferred into a 500 ml erlenmeyer flask containing 500 ml 0.5 M HAc at 20° C. (i.e., 15 ml glacial HAc in 500 ml water). The flask was put on a magnetic stirring device in the cold room (at 4° C.) spinning for 2 days. The cold collagen solution was centrifuged in the clinical centrifuge (top speed 1600×g or about 3000-4000 rpm) to sediment debris (10 min, 20°). The supernate from the clinical centrifuge was then placed in a test tube in an ultracentrifuge (Model L8-70) having a No. 40 rotor, and spun at about 40,000 rpm for about 42 hours at 4° C. A pellet about 1 cm thick formed from about 10 ml of supernate.

A pellet was fixed using a solution of 2% formaldehyde made from paraformaldehyde and 3% glutaraldehyde in 0.1 M Cacodylate buffer (available commercially from Aldrich Corporation). About 5 ml of the fixing solution was placed in the centrifuge tube with the pellet for about 30 min. at 4° C. After that the fixing solution was changed and the pellet placed in 5 ml of fresh fixing solution for about 30 minutes at 20° C. The pellet was washed with Tris (0.15M, pH 7.5) and with Cacodylate buffer. The native soluble collagen material, when ultracentrifuged, appeared to form a fairly large, white pellet at bottom of tube on initial fixation. When the pellet was cut from the tube, however, it became apparent that the pellet was really a large, *transparent* mass of collagen overlying the visible, white pellet. A 5 mm slice of the pellet was subjected to absorbance measurement, and exhibited less than about four percent absorbance over the range of wavelengths of from about 400 to 900 mm, as shown in FIG. 1. When cut with a razor blade, the pellet was tough, like cutting through a piece of leather.

EXAMPLE 2

An ultracentrifuged pellet of native soluble collagen was formed the same as in Example 1 except prior to the step of ultracentrifuging, the collagen solution was dialyzed against water, forming a clear gel. The gel was then transferred to a test tube for ultracentrifugation. A transparent pellet formed as in Example 1. When fixed, the pellet exhibited optical clarity and rigidity, and was leather-like in consistency.

EXAMPLE 3

Thin slices of the pellets formed in Examples 1 and 2 were examined by electron microscopy. The section of the pellet of Example 1 exhibited no apparent structure. The section of the pellet of Example 2 exhibited thin strand-like structures.

The present invention has been described in detail with reference to the preferred embodiments thereof. However, it is appreciated that those skilled in the art, upon consideration of the specification, may make modifications and improvements within the spirit and scope of the invention.

We claim:

1. A prosthetic cornea replacement comprising collagen wherein the collagen component consists essentially of a native, non-fibrillized, transparent, cross-linked collagen material that has less than 5% absorbance of light at 900 mm for a 5 nm thick cross section.

2. The cornea replacement of claim 1, wherein such replacement contains between 0.5 and 20% collagen protein.

3. The cornea replacement of claim 1, further comprising polyhydroxyethylmethacrylate or vitrosin, in a range of between 0.01 to 50% by weight.

4. A native, non-fibrilized, transparent collagen material formed from a soluble collagen solution by ultracentrifuging to form a pellet and fixing said pellet, said collagen material having less than 5% absorbance of light at 900 nm for a 5 mm thick sample and comprising polyhydroxyethylmethacrylate or vitrosin, in a range of from 0.01 to 50 percent by weight, based on the collagen protein.

* * * * *